(12) United States Patent  (10) Patent No.: US 6,710,943 B2
Weir  (45) Date of Patent: Mar. 23, 2004

(54) VIEWER FOR LASER-INSCRIBED DIAMONDS

(76) Inventor: David Alan Weir, 3200 Foothill Dr., #5, Thousand Oaks, CA (US) 91361

( * ) Notice: Subject to any disclaimer, the term of this patent is extended or adjusted under 35 U.S.C. 154(b) by 15 days.

(21) Appl. No.: 10/147,693

(22) Filed: May 17, 2002

(65) Prior Publication Data

US 2002/0171946 A1 Nov. 21, 2002

Related U.S. Application Data

(60) Provisional application No. 60/291,669, filed on May 18, 2001.

(51) Int. Cl.⁷ .............................................. G02B 27/02
(52) U.S. Cl. ...................... 359/803; 359/802; 359/813
(58) Field of Search ................... 359/802–804, 359/808, 813, 819; 356/30

(56) References Cited

U.S. PATENT DOCUMENTS

| | | | | |
|---|---|---|---|---|
| 4,577,927 A | * | 3/1986 | Raney | 359/803 |
| 4,906,083 A | * | 3/1990 | Sattler | 359/386 |
| 5,260,763 A | * | 11/1993 | Yamashita | 356/30 |
| 5,510,891 A | * | 4/1996 | Frangie | 356/30 |
| 6,211,484 B1 | * | 4/2001 | Kaplan et al. | 219/121.68 |
| 6,292,315 B1 | * | 9/2001 | Ravich et al. | 359/885 |
| 6,473,164 B1 | * | 10/2002 | De Jong et al. | 356/30 |

* cited by examiner

Primary Examiner—Jordan M. Schwartz
Assistant Examiner—Jessica Stultz
(74) Attorney, Agent, or Firm—Kelly Bauersfeld Lowry & Kelley, LLP

(57) ABSTRACT

A hand-held gemstone viewing scope includes a slidable armature movable relative to a base and defining a viewer housing a lens. A platform is rotatably connected to a top end of the base and configured to adjustably mount a gemstone or ring in line with the lens. A gem laser inscription is determined by mounting a ring or gemstone in line with the lens, moving the armature to focus the lens on the gemstone, and rotating the platform until the gem inscription is located.

17 Claims, 3 Drawing Sheets

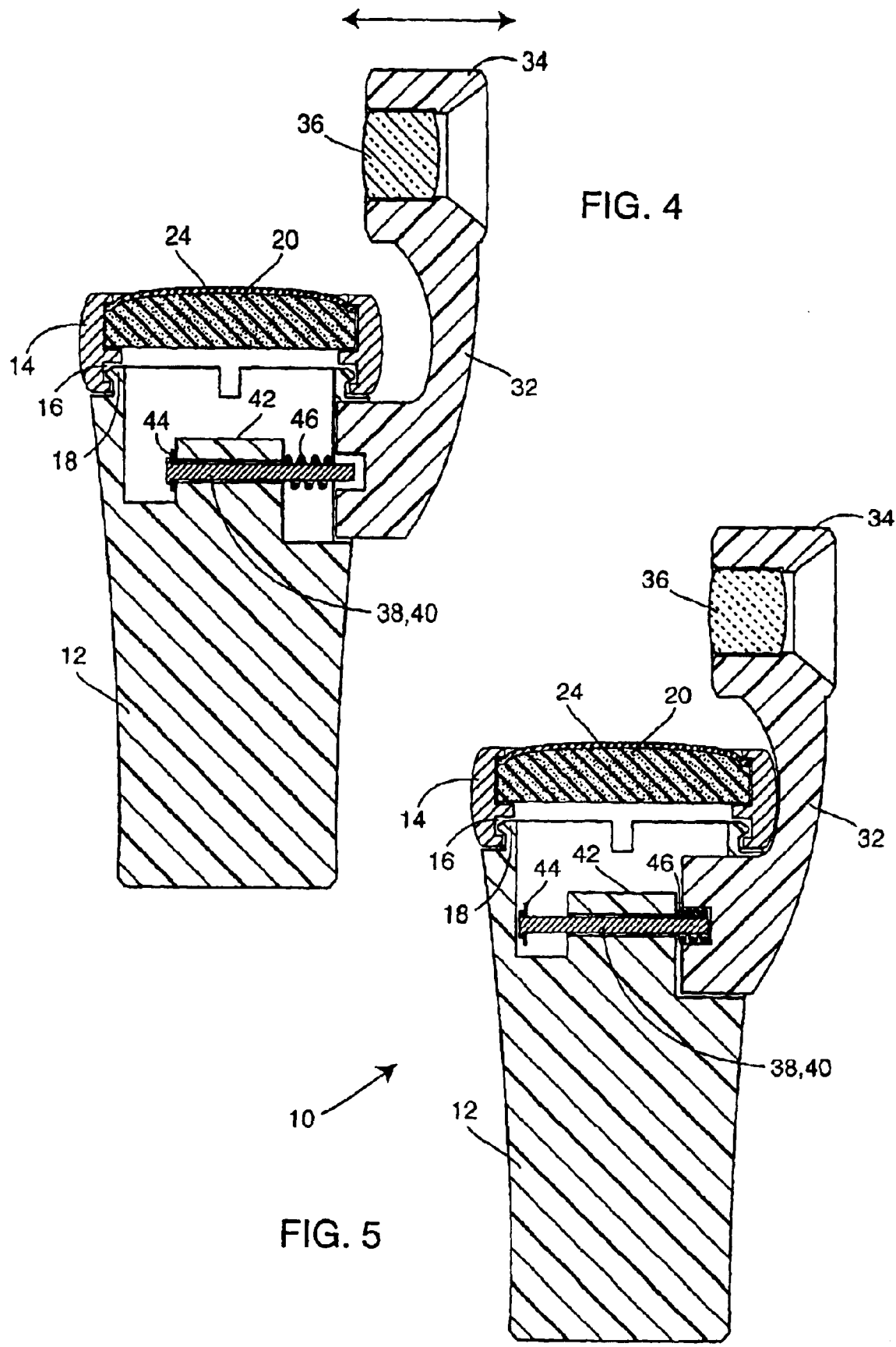

VIEWER FOR LASER-INSCRIBED DIAMONDS

RELATED APPLICATION

This application claims priority from U.S. Provisional Application Serial No. 60/291,669, filed May 18, 2001.

BACKGROUND OF THE INVENTION

The present invention generally relates to jewelry loupes and scopes. More particularly, the present invention relates to a hand-held gemstone viewing scope that allows viewing of laser-marked inscriptions of diamonds and other gemstones.

The process of using a laser to mark jewelry with inscriptions, certificate numbers, brand names, messages, etc. on the edge of diamonds and other gemstones has existed for a few years. Currently, the most common method for viewing and verifying the laser-mark inscription on the gemstone is to use a 10× power jewelers loupe. However, the text height of the laser inscription can be as small as 8 microns in height. Such jewelers loupes provide only minimal readability. It is also extremely difficult to locate and study the gemstone relative to the magnifying loupe, while holding the stone in one hand and the jewelers loupe in the other hand. This is particularly difficult for untrained individuals, such as consumers of jewelry.

Accordingly, there is a continuing need for a viewing scope which accommodates a loose gemstone or ring so that the laser inscriptions can be easily located and discerned. The present invention fulfills these needs and provides other related advantages.

SUMMARY OF THE INVENTION

The present invention resides in a hand-held gemstone viewing scope that allows a user thereof to easily locate, discern and view laser-marked inscriptions of diamonds, gemstones and the like. The viewing scope generally comprises a base and a viewer movably associated with the base and housing a lens. A platform is rotatably connected to a top end of the base and configured to adjustably mount a gemstone or ring in line with the lens. A gemstone and laser inscription is determined by mounting the ring or gemstone to the platform and moving the viewer to focus the lens on the gemstone. The platform is rotated, thus rotating the gemstone, until the gem inscription is located.

In a particularly preferred embodiment, an armature is attached to the base and extends above the base to define the viewer. Preferably, the armature includes a spring-loaded pin extending into the base and slidable with respect to the base for moving the armature relative to the base to focus the lens on the gemstone.

The platform typically comprises a ring platform having an inner circumferential channel that accepts an outer flange extending from the top end of the base so as to be rotatably connected to the base. A mounting member comprising a cushion is disposed within the ring platform. A ring-accepting slot is formed in the cushion for supporting the ring or mounted gemstone.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 4 is a cross-sectional view of the viewing scope taken generally along 4—4 of FIG. 2, illustrating an armature thereof in a fully extended position; and FIG. 5 is a cross-sectional side view similar to FIG. 4, illustrating the armature slid towards the base and platform of the viewing scope.

DETAILED DESCRIPTION OF THE PREFERRED EMBODIMENT

Figure 1:
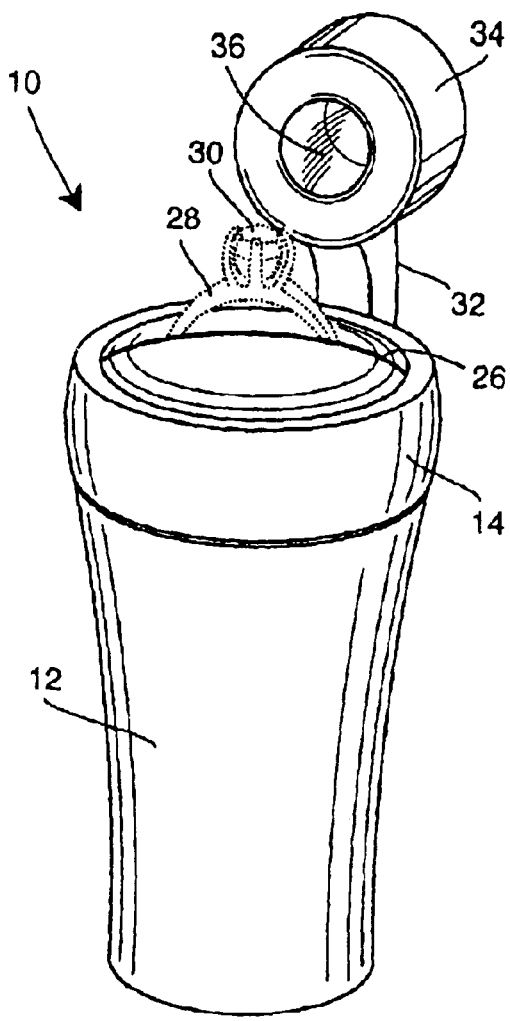
FIG. 1 is a perspective view of a hand-held gemstone viewing scope embodying the present invention and having a ring, in phantom, mounted therein for viewing.
Figure 2:
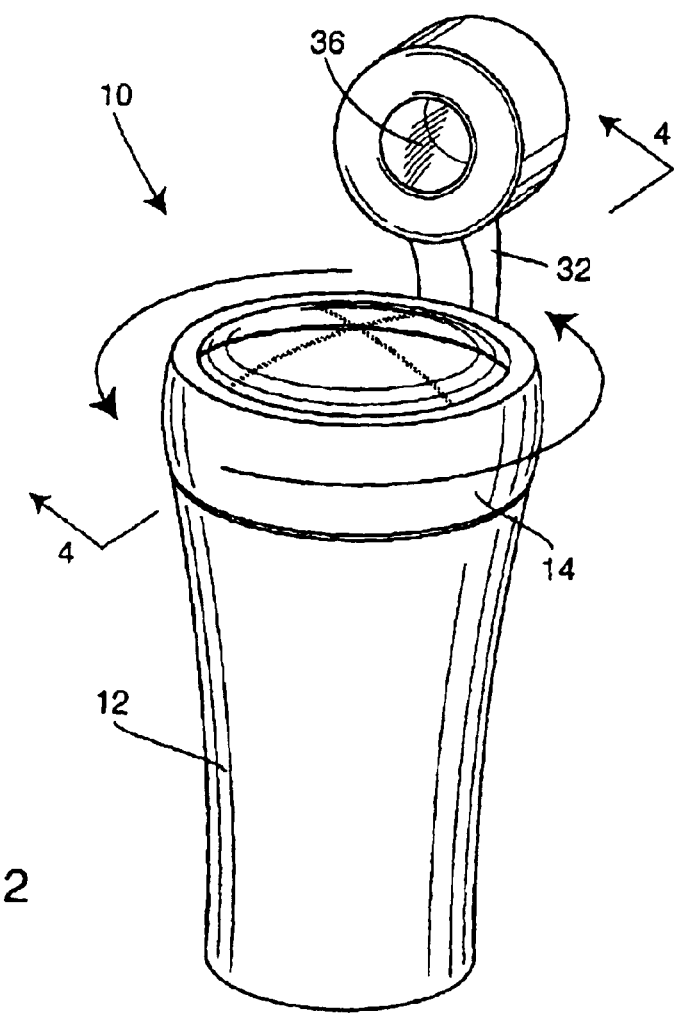
FIG. 2 is a perspective of the viewing scope of FIG. 1, illustrating the rotating nature of a ring platform of the viewing scope.

As shown in the accompanying drawings for purposes of illustration, the present invention resides in a hand-held gemstone viewing scope, generally referred to by the reference number 10. With reference to FIGS. 1 and 2, the viewing scope 10 includes a hand-held base 12 which is generally cylindrical and has a flat bottom surface for placement upon a table or the like to serve as a stand.

Figure 3:
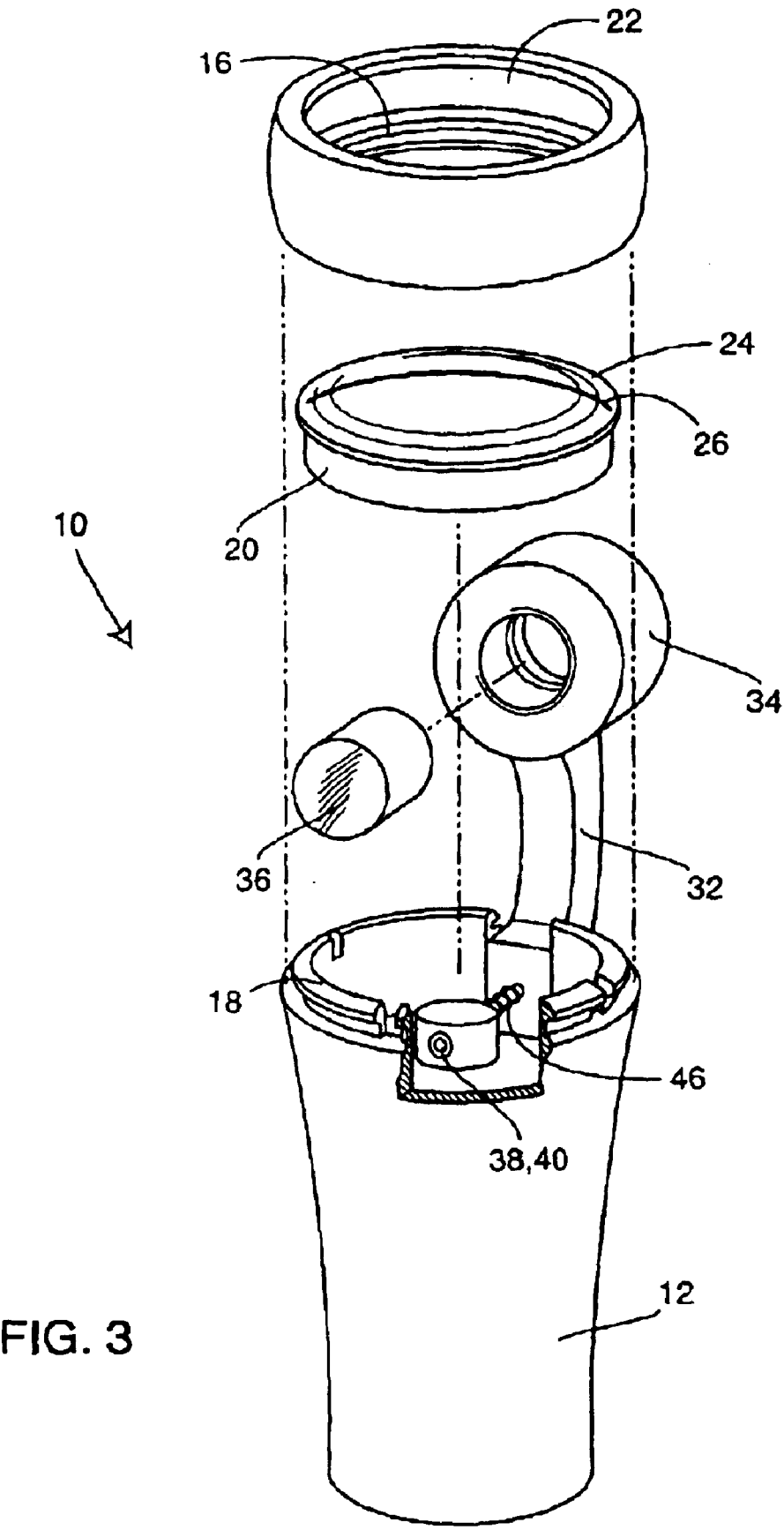
FIG. 3 is a partially fragmented and exploded perspective view of the viewing scope, illustrating the various component parts thereof.

A ring platform 14 is connected to a top end of the base 12 so as to rotate a full 360°, as illustrated in FIG. 2. As shown in FIGS. 3–5, the ring 14 includes a lower and inner circumferential channel 16 in a lower end thereof that snap-fits onto a flange 18 extending from the top end of the base 12. A circular cushion 20 comprised of a soft elastomeric material, such as foam, is disposed within the ring 14 and sized such so as to reside within an upper groove 22. Preferably, the cushion 20 includes an aesthetically pleasing velvet top surface 24. As shown in FIG. 1, the cushion and velvet covering 20 and 24 have a slot 26 cut therethrough for the insertion of a ring 28 bearing a gemstone 30, such as a diamond. Instead of the ring 28 the diamond or gemstone 30 can be loosely associated with a spring setting or the like. As the ring platform 14 is rotated, the cushion 20 and ring 28 are rotated as well.

An armature 32 extends from the base 12 to define a viewer 34 at an upper end thereof positioned above the platform 14 and having a major axis which is generally transverse to the longitudinal axis of the base 12. A lens 36 is mounted within the viewer 34 for magnifying the gemstone 30. Preferably, the lens 36 is a 20× power lens so as to sufficiently magnify the laser inscriptions. An aspheric triplet lens, such as a 20× Hastings triplet lens, has been found to be particularly useful as this lens counteracts distortion at a high magnification.

The armature 32 is movable with respect to the base 12. As illustrated in FIGS. 3–5, in a particularly preferred embodiment, this is accomplished by inserting a pin 38 through an aperture 40 extending through a central post 42. The end of the pin includes a stop 44 to prevent the pin from being pulled without the aperture 40. Thus, the armature 32 can be slid into the base 12 and away from the base 12 to focus the lens 36 upon the gemstone 30. Preferably, a spring 46 is disposed between the post 42 and the armature 32 and encircling the pin 38 so as to push the armature 32 away from the post 42 in a relaxed state.

In use, a ring 28 is inserted into the slot at a desired height such that the gemstone 30 is directly in line with the viewer 34 and lens 36. The slot 26 allows rings and settings of various sizes to be utilized as the ring or setting 28 can be vertically adjusted to the desired height. Also, the cushioned material 20 prevents scratching or marring of the finished surfaces of the ring 28. Laser inscriptions are typically formed on the edge or "girdle" of diamonds and other gemstones. Thus, this girdle or edge is brought into alignment with the lens 36. With the gemstone 30 stabilized and secured in place, a user looks through the viewer 34 and slides the armature 32 until the edge of the gemstone 30 is in focus. The diamond 30 is then rotated about its vertical axis by rotating the ring platform 14 with a thumb and forefinger until the inscriptions are located. Final focusing is achieved by moving armature 32 until the inscriptions can be determined and read.

The viewing scope 10 of the present invention provides many benefits over presently used jewelers loupes. The gemstone 30 is securely stabilized and held in place without the need of holding the gemstone in one's hand or tweezer-like devices. The gemstone 30 is easily adjusted in vertical height, and rotated to facilitate location of the inscriptions. Once found, the viewing scope 10 can be placed upon a surface, such as a table, and another individual can focus the lens 36 to view the inscriptions which are directly in front of the lens 36. The viewing scope 10 is not only easy to use, but utilizes materials and manufacturing procedures which render the viewing scope 10 relatively inexpensive to produce.

Although several embodiments have been described in detail for purposes of illustration, various modifications may be made without departing from the scope and spirit of the invention. Accordingly, the invention is not to be limited, except as by the appended claims.

What is claimed is:

1. A handheld gemstone viewing scope, comprising:
   a base;
   a viewer movably associated with the base and housing a lens;
   an armature attached to the base and extending above the base, an end of the armature defining the viewer, wherein the armature includes a spring-loaded pin extending into the base and slidable with respect to the base for moving the armature relative to the base; and
   a platform rotatably connected to a top end of the base and configured to adjustably mount a gemstone or ring directly in line with the lens;
   whereby a gem inscription is determined by mounting the ring or gemstone to the platform in line with the lens, moving the viewer to focus the lens on the gemstone, and rotating the platform to rotate the gemstone until the gem inscription is located.

2. The viewing scope of claim 1, wherein the platform comprises a ring platform rotatably connected to the base, and a mounting member within the ring platform.

3. The viewing scope of claim 2, wherein the mounting member comprises a cushion disposed within the ring platform and including a ring-accepting slot.

4. The viewing scope of claim 2, wherein the ring platform includes an inner circumferential channel that accepts an outer flange extending from the top end of the base.

5. The viewing scope of claim 2, wherein the lens is a aspheric triplet lens.

6. A handheld gemstone viewing scope, comprising:
   a base;
   an armature slidably attached to the base and extending above the base to define a viewer housing a lens, the armature including a spring-loaded pin extending into the base and slidable with respect to the base for moving the armature relative to the base; and
   a ring platform rotatably connected to a top end of the base and having a mounting member therein configured to adjustably mount a gemstone or ring directly in line with the lens;
   whereby a gem inscription is determined by mounting the ring or gemstone to the platform in line with the lens, sliding the armature relative to the base to focus the lens on the gemstone, and rotating the ring platform to rotate the gemstone until the gem inscription is located.

7. The viewing scope of claim 6, wherein the mounting member comprises a cushion disposed within the ring platform and including a ring-accepting slot.

8. The viewing scope of claim 6, wherein the ring platform includes an inner circumferential channel that accepts an outer flange extending from the top end of the base.

9. The viewing scope of claim 6, wherein the lens is a aspheric triplet lens.

10. A handheld gemstone viewing scope, comprising:
    a base;
    an armature having a spring-loaded pin extending into the base and slidable with respect to the base, the armature extending above the base to define a viewer housing a lens; and
    a ring platform rotatably connected to a top end of the base and having a cushion therein having a ring-accepting slot to adjustably mount a gemstone or ring directly in line with the lens;
    whereby a gem inscription is determined by mounting the ring or gemstone to the platform in line with the lens, sliding the armature relative to the base to focus the lens on the gemstone, and rotating the ring platform to rotate the gemstone until the gem inscription is located.

11. The viewing scope of claim 10, wherein the ring platform includes an inner circumferential channel that accepts an outer flange extending from the top end of the base.

12. The viewing scope of claim 10, wherein the lens is a aspheric triplet lens.

13. A gemstone viewing scope, comprising:
    a handheld base;
    an armature extending vertically upwardly from the base;
    a viewer associated with the armature and housing a lens, wherein the viewer is movable horizontally relative to the base; and
    a platform rotatably connected to a top end of the base and configured to adjustably mount a gemstone or ring directly in line with the lens;
    whereby a gem inscription is determined by mounting the ring or gemstone to the platform in line with the lens, moving the viewer to focus the lens on the gemstone, and rotating the platform to rotate the gemstone until the gem inscription is located.

14. The viewing scope of claim 13, wherein the armature includes a spring-loaded pin extending into the base and slidable with respect to the base for moving the armature relative to the base.

15. The viewing scope of claim 13, wherein the platform comprises a ring platform rotatably connected to the base, and a mounting member within the ring platform.

16. The viewing scope of claim 15, wherein the mounting member comprises a cushion disposed within the ring platform and including a ring-accepting slot.

17. The viewing scope of claim 15, wherein the ring platform includes an inner circumferential channel that accepts an outer flange extending from the top end of the base.

* * * * *